(12) United States Patent
Dussarrat et al.

(10) Patent No.: US 7,064,083 B2
(45) Date of Patent: *Jun. 20, 2006

(54) HEXAKIS(MONOHYDROCARBYLAMINO)- DISILANES AND METHOD FOR THE PREPARATION THEREOF

(75) Inventors: Christian Dussarrat, Ibaraki (JP); Jean-Marc Girard, Paris (FR)

(73) Assignee: L'Air Liquide, Societe Anonyme a Directoire et Conseil de Surveillance pour l'Etude et l'Exploitation des Procedes Georges Claude, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/222,361

(22) Filed: Sep. 8, 2005

(65) Prior Publication Data

US 2006/0030724 A1    Feb. 9, 2006

Related U.S. Application Data

(63) Continuation of application No. 10/497,399, filed as application No. PCT/EP02/13790 on Nov. 27, 2002.

(30) Foreign Application Priority Data

Nov. 30, 2001   (JP) .............................. 2001-367123

(51) Int. Cl.
    *H01L 21/31*    (2006.01)
(52) U.S. Cl. ...................... 438/769; 438/791; 438/786; 438/778

(58) Field of Classification Search ................ 438/769, 438/791, 786, 778
See application file for complete search history.

(56) References Cited

OTHER PUBLICATIONS

International Search Report for PCT/EP02/13790.
Chemical Abstracts Service; Schuh, Heinz et al: "Disilanylamines. Compounds comprising the structural unit silicon-silicon-nitrogen, as single-source precursors for plasma-enhanced chemical vapor deposition (PE-CVD) of silicon nitride".
Chemical Abstracts Service; Wrackmeyer, Bernd et al: "Carbon-13, nitrogen-15 and silicon-29 nuclear magnetic resonance studies of some aminosilanes and aminodisilanes".

*Primary Examiner*—Samuel Barts
(74) *Attorney, Agent, or Firm*—Linda K. Russell

(57) ABSTRACT

A composition and method of preparation, to provide silane compounds that are free of chlorine. The compounds are hexakis(monohydrocarbylamino)disilanes with general formula (I)

$$((R)HN)_3\text{—Si—Si—}(NH(R))_3 \qquad (I)$$

wherein each R independently represents a $C_1$ to $C_4$ hydrocarbyl. These disilanes may be synthesized by reacting hexachlorodisilane in organic solvent with at least 6-fold moles of the monohydrocarbylamine $RNH_2$ (wherein R is a $C_1$ to $C_4$ hydrocarbyl). Such compounds have excellent film-forming characteristics at low temperatures. These films, particularly in the case of silicon nitride and silicon oxynitride, also have excellent handling characteristics.

3 Claims, 1 Drawing Sheet

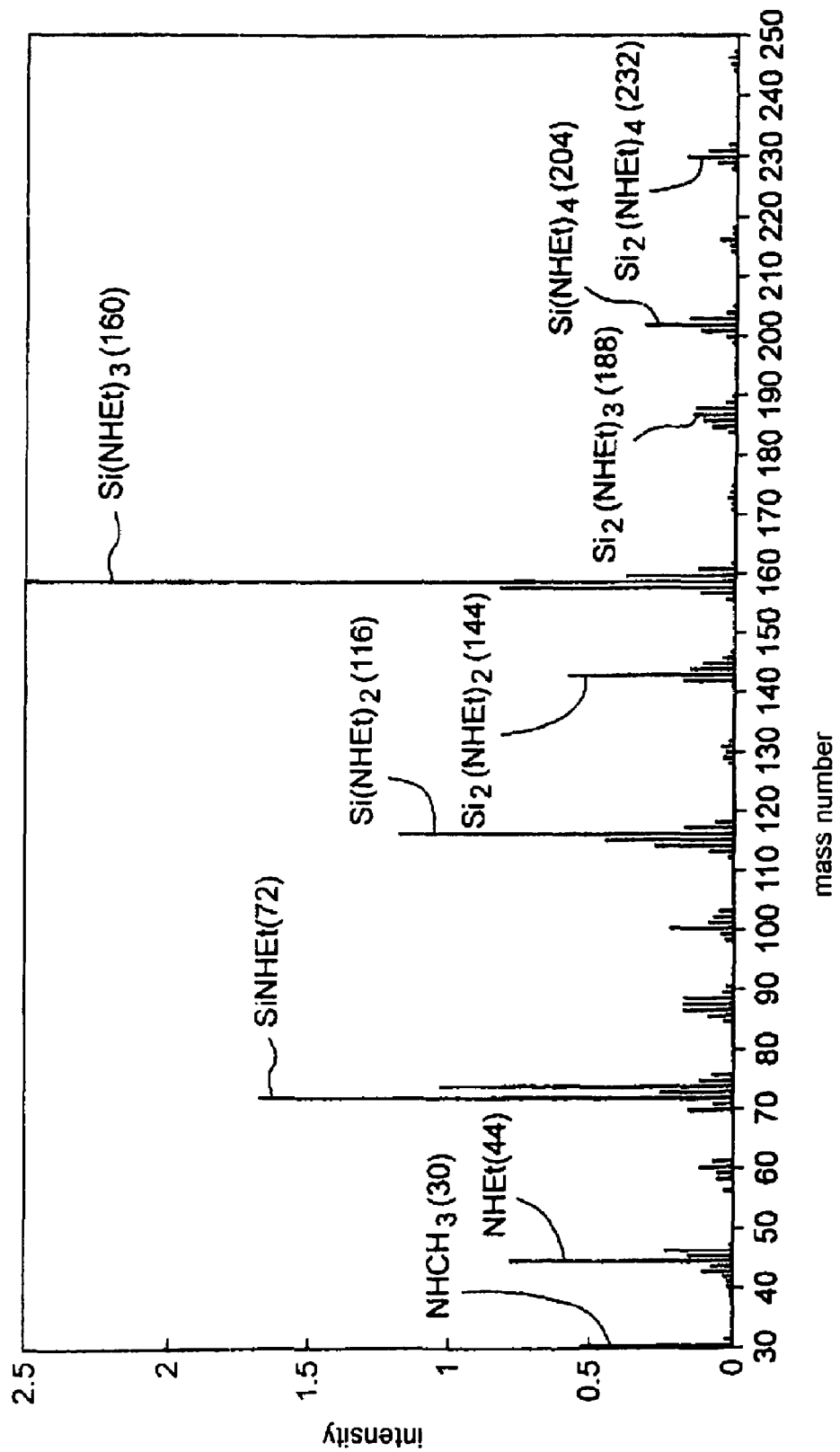

US 7,064,083 B2

HEXAKIS(MONOHYDROCARBYLAMINO)-DISILANES AND METHOD FOR THE PREPARATION THEREOF

This application is a continuation of application Ser. No. 10/497,399, filed on Dec. 27, 2004 which is a 371 of PCT/EP02/13790, filed Nov. 27, 2002.

BACKGROUND OF THE INVENTION

This invention relates to disilane compounds and to a method for their preparation. More particularly, this invention relates to hexakis(monohydrocarbylamino) disilanes and to a method for the preparation thereof.

Silane compounds such as monosilanes and disilanes are used in a variety of applications. In the field of semiconductors, silane compounds are frequently used as starting materials for the production by chemical vapor deposition (CVD) of silicon-based dielectric films of, e.g., silicon nitride, silicon oxide, or silicon oxynitride. More specifically, silane compounds can produce silicon nitride by reaction with a nitrogen-containing reaction gas such as ammonia, silicon oxide by reaction with an oxygen-containing gas such as oxygen, and silicon oxynitride by reaction with a nitrogen-containing gas and an oxygen-containing gas.

At present the standard method for producing silicon nitride films by CVD involves inducing a reaction between ammonia gas and dichlorosilane (=the silane compound); however, ammonium chloride is produced as a by-product by this reaction. Ammonium chloride is a white solid and as such accumulates in and clogs the—exhaust lines of the CVD reaction apparatus. A CVD method is therefore required in which the starting material is a chlorine-free silane compound. It is also desirable during the production of silicon nitride, etc., by CVD technology to obtain good film—deposition rates at low temperatures (at or below 600° C.).

Tetrakis(dimethylamino)silane and tetrakis(diethylamino) silane have been examined as chlorine-free silane compounds, but these aminosilane compounds suffer from the problem of providing slow film—deposition rates at low temperatures.

The chlorine-free alkylaminodisilanes are also known. These alkylaminodisilanes are solids at ambient temperatures. For example, -hexakis(dimethylamino)disilane is reported to undergo sublimation at 230° C. under reduced pressure. Compounds that are solids at ambient temperature have poor handling characteristics.

An object of this invention, therefore, is to provide novel silane compounds that are free of chlorine, that provide excellent film—depositing characteristics at low temperatures in the case of silicon nitride films, etc., and that also have excellent handling characteristics. An additional object of this invention is to provide a method for preparing these novel silane compounds.

SUMMARY

The first aspect of this invention provides hexakis(monohydrocarbylamino) isilanes with general formula (I)

  (I)

wherein each R independently represents $C_1$ to $C_4$ hydrocarbyl.

The second aspect of this invention provides a method for the preparation of the hexakis(monohydrocarbylamino)disilanes (I), said method being characterized by reacting hexachlorodisilane in organic solvent with at least 6-fold moles of the monohydrocarbylamine $RNH_2$ (wherein R is $C_1$ to $C_4$ hydrocarbyl).

BRIEF DESCRIPTION OF THE DRAWING

For a further understanding of the nature and objects for the present invention, reference should be made to the following detailed description, taken in conjunction with the accompanying drawing, in which like elements are given the same or analogous reference numbers and wherein:

FIG. 1 illustrates the mass spectrum of one embodiment of the invention.

DESCRIPTION OF PREFERRED EMBODIMENTS

This invention will be described in additional detail hereinbelow.

The compounds of this invention are hexakis(monohydrocarbylamino)disilanes with general formula (I).

  (I)

Each R in (I) is independently selected from $C_1$ to $C_4$ hydrocarbyl. This $C_1$ to $C_4$ hydrocarbyl includes the vinyl group and $C_1$ to $C_4$ alkyl such as methyl, ethyl, propyl, isopropyl, butyl, and tert-butyl. The six R groups in (I) may all be the same or may differ from one another. The six R groups are preferably the same viewed from the perspective of ease of preparation, and within the context of this invention all of the R groups are preferably ethyl. Thus, hexakis(monoethylamino)disilane is a preferred disilane according to this invention.

Disilanes with formula (I) can be synthesized by reacting hexachlorodisilane ($Cl_3$—Si—Si—$Cl_3$) in organic solvent with at least 6-fold moles of the monohydrocarbylamine $RNH_2$ (R=$C_1$ to $C_4$ hydrocarbyl). The monohydrocarbylamine for reaction with hexachlorodisilane includes, inter alia, methylamine, ethylamine, propylamine, isopropylamine, tert-butylamine, and vinylamine. The monohydrocarbylamine used can take the form of a single monohydrocarbylamine or a mixture of monohydrocarbylamines. However, the use of a single monohydrocarbylamine is preferred viewed from the perspective of ease of preparation, and the use of ethylamine is even more preferred.

As specified above, the hexachlorodisilane and monohydrocarbylamine are reacted with each other using at least 6 moles of the latter per 1 mole of the former. However, the use of a large excess of the monohydrocarbylamine over hexachlorodisilane is preferred for the purpose of inhibiting the production of N-hydrocarbyldisilazane. In specific terms, the use of a hexachlorodisilane:monohydrocarbylamine molar ratio of 1:12 to 1:36 is preferred. Use of at least 12 moles monohydrocarbylamine per 1 mole hexachlorodisilane also enables trapping, as the monohydrocarbylamomium chloride (solid), of the hydrogen chloride (6 moles) that is produced as a by-product in the reaction. This monohydrocarbylamomium chloride can be easily removed from the reaction mixture post-reaction by filtration.

Organic solvent is used as the reaction solvent for reaction of the hexachlorodisilane and monohydrocarbylamine. This organic solvent encompasses tetrahydrofuran and straight-chain and cyclic hydrocarbons, for example, pentane, hexane, and octane. Pentane is the preferred solvent.

The reaction between hexachlorodisilane and monohydrocarbylamine is preferably run at a temperature from −30° C. to +50° C. In general, this reaction will be run by first bringing the reaction solvent to a temperature in the preferred range of −30° C. to +50° C., adding/dissolving the monohydrocarbylamine in the reaction solvent, and then gradually adding the hexachlorodisilane, for example, by dropwise addition. The hexachlorodisilane can be dropped in either pure or dissolved in the same solvent as the reaction solvent. The reaction is subsequently run for 2 to 24 hours while stirring the reaction solvent and holding at the aforementioned temperature. After this period of stirring, the reaction solvent is heated to room temperature (approximately 20° C. to 50° C.) and stirring is preferably continued for at least another 10 hours. The hydrocarbylammonium chloride, a solid by-product, is then filtered off and the solvent and residual amine are distilled off in vacuo. The resulting hexakis(monohydrocarbylamino)disilane can be subjected to additional purification by fractional distillation.

The hexakis(monohydrocarbylamino)disilanes according to this invention are liquids at ambient temperatures (approximately 20° C. to 50° C.), do not contain chlorine, and are highly reactive and support excellent silicon nitride and silicon oxynitride film deposition rates at low temperatures (no greater than 600° C.). Their high reactivity is caused by the bonding of the monohydrocarbylamino group to the silicon and by the weak Si—Si direct bond.

The hexakis(monohydrocarbylamino)disilanes according to this invention can therefore, in view of the properties described above, be used in the semiconductor sector as starting materials (precursors) for the fabrication by thermal CVD of the silicon nitride and silicon oxynitride used, inter alia, as dielectric films.

For example, a silicon nitride film can be formed on a semiconductor substrate by introducing at least one semiconductor substrate into a reaction chamber, introducing thereinto a hexakis(monohydrocarbylamino)disilane according to this invention and a nitrogen-containing gas (e.g., ammonia, hydrazine, an alkylhydrazine compound, or hydrogen azide), and inducing reaction between the hexakis (monohydrocarbylamino)disilane and the nitrogen-containing gas by heating.

An oxygen-containing gas (e.g., NO, $N_2O$, $NO_2$, $O_2$, $O_3$, $H_2O$, $H_2O_2$) can of course also be introduced into the reaction chamber, in which case a silicon oxynitride film will be formed on the semiconductor substrate by reaction of the hexakis(monohydrocarbylamino)disilane, nitrogen-containing gas, and oxygen-containing gas.

EXAMPLES

This invention is explained in greater detail by the working examples provided below, but this invention is not limited to these working examples.

Example 1

Synthesis of hexakis(monoethylamino)disilane (HEAD)

Pentane was used as the reaction solvent and was cooled to 0° C. for the reaction. An ethylamine solution was prepared by adding ethylamine (70 g, 1.55 mol) cooled to 0° C. to the cold pentane. Hexachlorodisilane (26.9 g, 0.1 mol) was added dropwise to this ethylamine solution. The resulting reaction solution was thereafter stirred for 2 hours at 0° C. and then for an additional 15 hours at room temperature (20° C.). The ethylammonium chloride by-product was filtered off and the pentane and ethylamine were distilled out in vacuo. 22.4 g of HEAD was obtained (yield=70%).

Results of Analysis $^1$H-NMR ($C_6D_6$, 500 MHz): $\delta$=0.61 ppm (broad, —NH), $\delta$=1.1 ppm (triplet, —$CH_3$), $\delta$=2.95 (pentet, —$CH_2$)

$^{13}$C-NMR ($C_6D_6$, 125 MHz): 20.7 ppm and 36.1 ppm (—$CH_2$—$CH_3$)

A signal assignable to the SiH bond was not observed in these NMR analyses.

FIG. 1 reports the analytical results (spectrum) from QMS (m/e<250) (Et=ethyl in FIG. 1). While the Si—Si bond was present in a number of fragments, for the sake of simplicity assignments are given only for main peaks.

The chlorine content of the synthesized HEAD product, as measured by ion chromatography, was no greater than trace levels. The melting point of the HEAD product was estimated at to be about 10° C.

Example 2

Production of Silicon Nitride Film Using HEAD

This example used the HEAD synthesized in Example 1. The various gases were introduced under the conditions given below into a reaction chamber loaded with a silicon substrate. A silicon nitride film was formed on the silicon substrate by running a CVD reaction at the reaction temperature given below. The HEAD was vaporized in a vaporizer while being mixed with nitrogen gas.

Gaseous HEAD flow rate: 5 sccm
ammonia gas flow rate: 50 sccm
carrier gas (nitrogen) flow rate: 60 sccm
pressure within the reaction chamber: 0.5 Torr
reaction chamber temperature: 550° C.

A silicon nitride film with a thickness of 900 Å was obtained in about 45 minutes as a result (silicon nitride film deposition rate=20 Å/minute). This silicon nitride film had a composition of $Si_{1.5}N_1$ according to analysis by Auger electron spectroscopy.

Example 3

Production of Silicon Oxynitride Film Using HEAD

This example used the HEAD synthesized in Example 1. The various gases were introduced under the conditions given below into a reaction chamber loaded with a silicon substrate. A silicon oxynitride film was formed on the silicon substrate by running a CVD reaction at the reaction temperature given below. The HEAD was vaporized in a vaporizer while being mixed with nitrogen gas.

Gaseous HEAD flow rate: 2 sccm
ammonia gas flow rate: 50 sccm
oxygen gas flow rate: 1 sccm
carrier gas (nitrogen) flow rate: 60 sccm
pressure within the reaction chamber: 0.5 Torr
reaction chamber temperature: 550° C.

A silicon oxynitride film with a thickness of approximately 2,000 Å was obtained in about 100 minutes as a result (silicon oxynitride film deposition rate=20 Å/minute). This silicon oxynitride film had a composition of $SiN_{0.42}O_{0.35}$ according to analysis by Auger electron spectroscopy.

As has been described above, this invention provides silane compounds that are free of chlorine, that provide excellent film—deposition characteristics at low temperatures in the case of silicon nitride films and silicon oxynitride films, and that also have excellent handling characteristics.

This invention also provides a method for producing these silane compounds. The hexakis(monohydrocarbylamino) disilanes of this invention are particularly useful in the semiconductor field for the formation by thermal CVD of the silicon nitride and silicon oxynitride used as dielectric films.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method of forming a silicon nitride film on a semiconductor substrate comprising:
   (a) introducing into a reaction chamber:
      1) at least one said substrate;
      2) a hexakis(monohydrocarbylamino)disilane with general formula (I)

$$((R)HN)_3\text{—}Si\text{—}Si\text{—}(NH(R))_3 \qquad (I)$$

wherein each R independently represents a $C_1$ to $C_4$ hydrocarbyl group; and
      3) a nitrogen containing gas; and
   (b) inducing a reaction between said hexakis(monohydrocarbylamino)disilane and said gas.

2. The method of claim 1, wherein said reaction is induced by heating.

3. The method of claim 2, wherein said heating is performed slowly.

* * * * *